(12) United States Patent
Moss et al.

(10) Patent No.: US 11,992,476 B2
(45) Date of Patent: *May 28, 2024

(54) TRANSDERMAL PSYCHOACTIVE ALKALOID COMPOSITION AND PREPARATION THEREOF

(71) Applicant: PSILO SCIENTIFIC LTD, Vancouver (CA)

(72) Inventors: Ryan Moss, Vancouver (CA); Benjamin Lightburn, Vancouver (CA); Lisa Ranken, Lake Country (CA)

(73) Assignee: PSILO SCIENTIFIC LTD, Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 18/259,697

(22) PCT Filed: Nov. 29, 2021

(86) PCT No.: PCT/CA2021/051702
§ 371 (c)(1),
(2) Date: Jun. 28, 2023

(87) PCT Pub. No.: WO2022/140842
PCT Pub. Date: Jul. 7, 2022

(65) Prior Publication Data
US 2023/0390213 A1    Dec. 7, 2023

Related U.S. Application Data

(60) Provisional application No. 63/139,453, filed on Jan. 20, 2021, provisional application No. 63/131,028, filed on Dec. 28, 2020.

(30) Foreign Application Priority Data

Jul. 1, 2021    (CA) .................................. CA 3123774

(51) Int. Cl.
| A61K 9/70 | (2006.01) |
| A61K 9/00 | (2006.01) |
| A61K 9/08 | (2006.01) |
| A61K 9/20 | (2006.01) |
| A61K 31/355 | (2006.01) |
| A61K 31/375 | (2006.01) |
| A61K 31/4045 | (2006.01) |
| A61K 31/405 | (2006.01) |
| A61K 31/675 | (2006.01) |
| A61K 36/07 | (2006.01) |
| A61K 45/06 | (2006.01) |
| A61K 47/10 | (2017.01) |
| A61K 47/12 | (2006.01) |

(52) U.S. Cl.
CPC ........ *A61K 31/4045* (2013.01); *A61K 9/0053* (2013.01); *A61K 9/0078* (2013.01); *A61K 9/08* (2013.01); *A61K 9/2095* (2013.01); *A61K 9/7023* (2013.01); *A61K 31/355* (2013.01); *A61K 31/375* (2013.01); *A61K 31/405* (2013.01); *A61K 31/675* (2013.01); *A61K 36/07* (2013.01); *A61K 45/06* (2013.01); *A61K 47/10* (2013.01); *A61K 47/12* (2013.01); *A61K 2236/15* (2013.01); *A61K 2236/17* (2013.01); *A61K 2236/39* (2013.01); *A61K 2236/53* (2013.01)

(58) Field of Classification Search
None
See application file for complete search history.

(56) References Cited

U.S. PATENT DOCUMENTS

| 3,183,172 | A | 5/1965 | Roger |
| 5,550,166 | A | 8/1996 | Ostlund |
| 8,846,075 | B2 | 9/2014 | Jonsson |
| 9,308,175 | B2 | 4/2016 | Pellikaan |
| 11,298,388 | B2 | 4/2022 | Lightburn et al. |
| 11,331,357 | B2 | 5/2022 | Lightburn et al. |
| 2017/0157343 | A1 | 6/2017 | Davidson |

(Continued)

FOREIGN PATENT DOCUMENTS

| CA | 2339353 | 4/2000 |
| CA | 2794734 | 10/2011 |

(Continued)

OTHER PUBLICATIONS

Mroczek, T., et al., "Optimization of Extraction of Pyrrolizidine Alkaloids From Plant Material," Chem. Anal. (Warsaw), 51: 567-580 (2006). (Year: 2006).*
Passie, T. et al. The Pharmacology of Psilocybin. Addiction Biology 2002, vol. 7, pp. 357-364, E-ISSN 1369-1600.
Zhang et al, Chinese Journal of Chemical Engineering, Jun. 18, 2007 (Jun. 18, 2007), vol. 15(6), pp. 872-876, [online] [retrived on Apr. 25, 2022. Retrived from the internet: <https://www.sciencedirect.com/science/article/abs/pii/S1004954108600178>.
Abhijee et al. Recent Advancement in Emulgel: A novel Approach for Topical Drug Delivery, International Journal of Advances in Pharmaceutics 2017; 06(01);17-23 E-ISSN: 2320-4923; P-ISSN: 2320-4931.1.
Kaufman; U.S. Appl. No. 63/109,912, filed Nov. 5, 2020.

(Continued)

*Primary Examiner* — David J Blanchard
*Assistant Examiner* — Daniel F Coughlin
(74) *Attorney, Agent, or Firm* — Mintz, Levin, Cohn, Ferris, Glovsky and Popeo, P.C.

(57) ABSTRACT

A transdermal psychoactive alkaloid composition including a psychoactive alkaloid extract or synthetic psychoactive alkaloid. The alkaloids in the extract are predominantly dephosphorylated rather than phosphorylated. The transdermal psychoactive alkaloid composition also includes an alcohol carrier, a permeation enhancer, a thickener or gelling agent, and optional further excipients. A process for obtaining a transdermal psychoactive alkaloid composition includes dephosphorylating the alkaloid during extraction, purifying the extracted alkaloid, and standardizing it to a specific concentration by adding measured quantities of excipients.

17 Claims, 2 Drawing Sheets

(56) References Cited

U.S. PATENT DOCUMENTS

| | | | |
|---|---|---|---|
| 2019/0142851 A1 | 5/2019 | Chadeayne | |
| 2020/0375967 A1 | 12/2020 | Stamets | |
| 2022/0054402 A1 | 2/2022 | Kaufman | |

FOREIGN PATENT DOCUMENTS

| | | |
|---|---|---|
| CA | 3050679 | 7/2018 |
| CA | 3052974 | 8/2018 |
| CA | 3078765 | 4/2019 |
| CA | 3088384 | 10/2020 |
| CA | 3137106 | 10/2020 |
| CA | 3097246 | 11/2021 |
| CN | 101292727 | 10/2008 |
| DE | 264023 | 1/1989 |
| GB | 911946 | 12/1962 |
| WO | 03074526 | 9/2003 |
| WO | 2016161138 | 10/2016 |
| WO | 2020157569 | 8/2020 |
| WO | 2021003467 | 1/2021 |
| WO | 2021007152 | 1/2021 |

OTHER PUBLICATIONS

Anastos N. et al., "The Determination of Psilocin and Psilocybin in Hallucinogenic Mushrooms by HPLC Utilizing a Dual Reagent Acidic Potassium Permanganate and Tris(2,20-bipyridyl)ruthenium(II) Chemiluminescence Detection System", J Forensic Sci 51(1): 45-51 (2006).

Casale JF. An aqueous-organic extraction method for the isolation and identification of psilocin from hallucinogenic mushrooms. J Forensic Sci. Jan. 1985; 30(1):247-50.

De Boer P, "Simple method of psilocybin extraction", Blog: Fresh Truffles and Growkits Jun. 24, 2017 (Jun. 24, 2017).

Gartz, Extraction and analysis of indole derivatives from fungal biomass. Journal of Basic Microbiology 34(1): 17-22 (1994).

Kunle et al, Standardization of herbal medicines—a review, Int. J. Biodivers. Conserv. 4(3): 101-112 (2012).

Kysilka and Wurst, "A novel extraction procedure for psilocybin and psilocin determination in mushroom samples", Planta Medica 56(3): 327-328 (1990).

Mikey's Psilly Ethanol Extract (2017).

Moldavan et al., The effect of Psilocybe cubensis extract on hippocampal neurons in vitro, Fiziol Zh. 47(6): 15-23 (2001).

Nguyen et al., Optimization of Spray Drying Condition from Trametes Versicolor Mushroom Extract. Journal of Science and Technology 39A: 25-30 (2019).

Perkal, M., et al. "Determination of hallucinogenic components of Psilocybe mushrooms using high-performance liquid chromatography." J. Chromatography A 196 (1980), pp. 180-184.

Poliwoda et al., Determination of muscimol and ibotenic acid in mushrooms of Amanitaceae by capillary electrophoresis. Electrophoresis 35(18):2593-2599 (2014).

Psilocybin Expert, "Formulating New "Magic Mushroom" compositions", Psilocybin Technology, Feb. 13, 2018 (Feb. 13, 2018).

Roderick, "Psilocybin and Cannabis Cocktails", Pillow website, Dec. 29, 2019 (Dec. 29, 2019).

Uneasy1, "Psilocin HCl extraction" Chemistry mdma hiveboard (2003). Https://chemistry.mdma.ch/hiveboard/tryptamine/000448065.html.

Mahmoudi E, et al. Alteration of depressive-like behaviors by psilocybe cubensis alkaloid extract in mice: The role of glutamate pathway. Research Joural of Pharmacognosy 5(2): 17-24 (2018).

Adejoke HT, et al. A review on classes, extraction, purification and pharmaceutical imporlance of plants alkaloid. Journal of Medicinal and Chemical Sciences. 2019; 2:130-9.

Kysilka R. Chromatographic determination of psilocybin and psilocin in fruit bodies and mycelia of hallucinogenic mushrooms. Chem Listy (1990) 84:988-992 (in Czech). with English translation.

Lenz C, et al. Injury-Triggered Blueing Reactions of Psilocybe "Magic" Mushrooms. Angew Chem Int Ed Engl. Jan. 20, 2020;59(4):1450-1454. Epub Dec. 4, 2019.

Zhuk O, et al. Research on acute toxicity and the behavioral effects of methanolio extract from psilocybin mushrooms and psilocin in mice. Toxins (Basel). Mar. 27, 2015:7(4):1018-29.

* cited by examiner

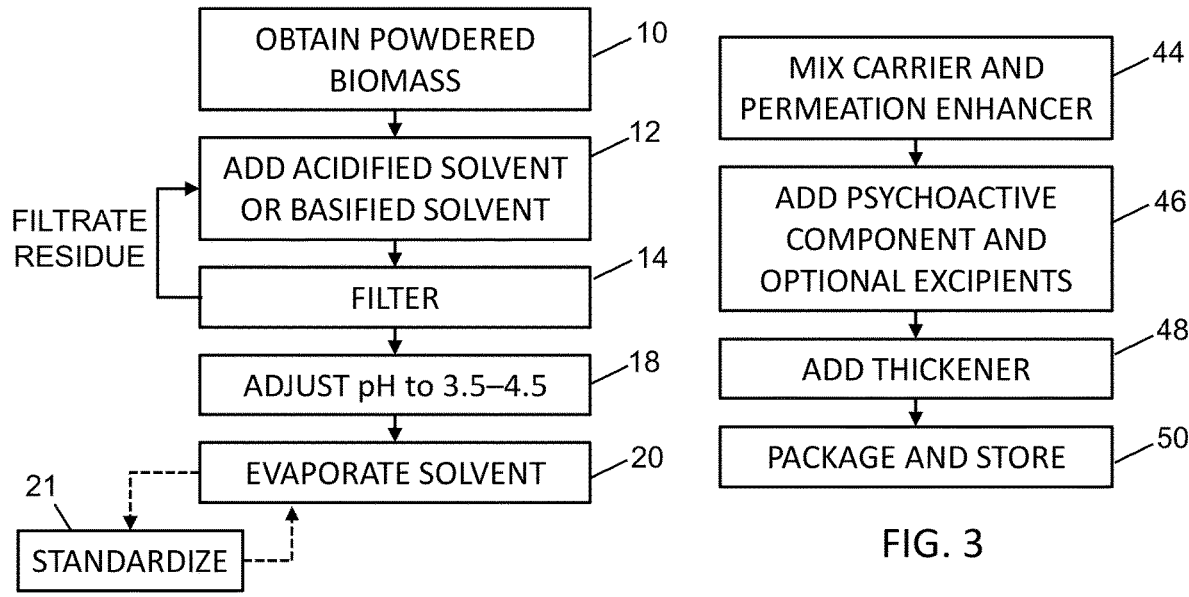
FIG. 1
FIG. 3
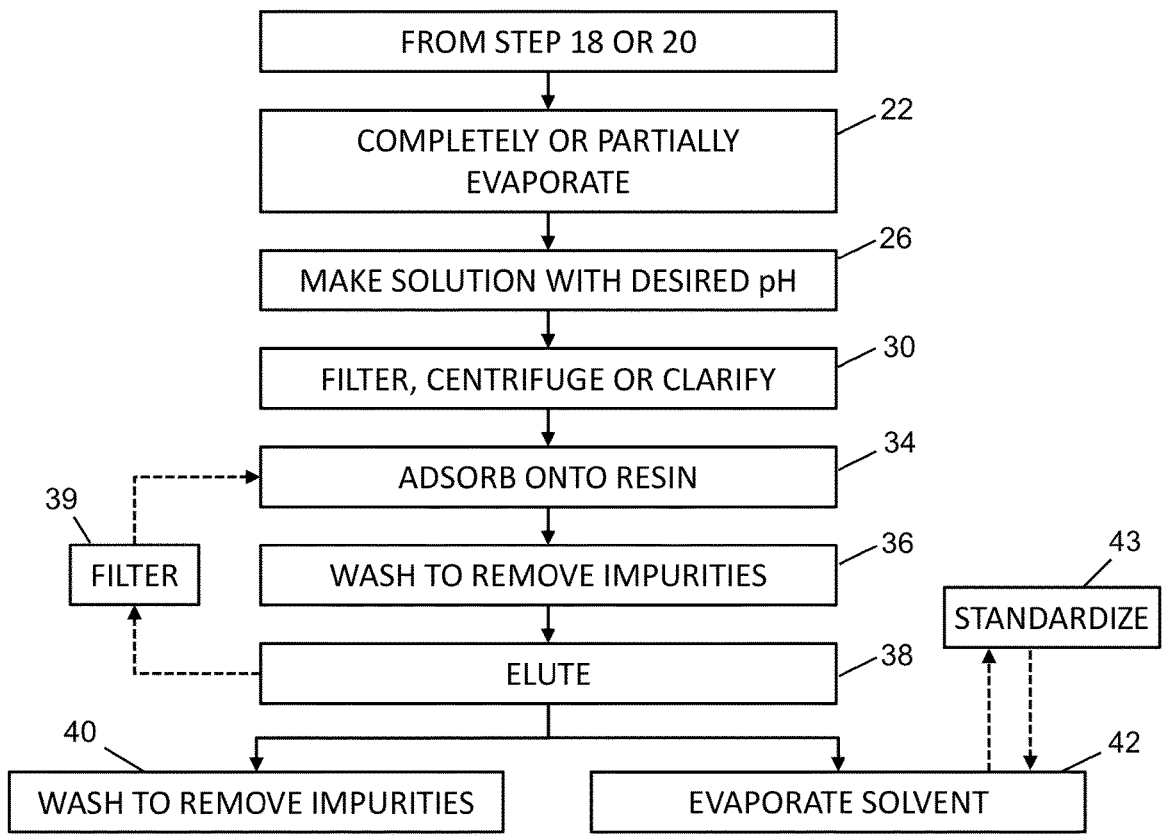
FIG. 2

TRANSDERMAL PSYCHOACTIVE ALKALOID COMPOSITION AND PREPARATION THEREOF

RELATED APPLICATIONS

This application is a U.S. National Phase Application of International Application No. PCT/CA2021/051702, filed Nov. 29, 2021, which claims the benefit of U.S. Provisional Application No. 63/131,028, filed Dec. 28, 2020, and U.S. Provisional Application No. 63/139,453, filed Jan. 20, 2021. PCT/CA2021/051702 further claims priority to and claims the benefit of Canadian Patent Application No. 3,123,774, filed Jul. 1, 2021. The content of each of the aforementioned patent applications is incorporated by reference in its entireties and for all purposes.

TECHNICAL FIELD

This application relates to a transdermal composition. More specifically, the present invention relates to a transdermal composition of psychoactive alkaloids. The present invention also relates to a process for preparing the transdermal composition.

BACKGROUND

A psychoactive substance is a chemical substance that changes brain function and results in alterations in perception, mood, consciousness, cognition, or behavior. The psychoactivity of these substances may include sedative, stimulant, euphoric, deliriant, and hallucinogenic effects. These substances have been used recreationally, to purposefully improve performance or alter one's consciousness, and as entheogens for ritual, spiritual, or shamanic purposes. Some categories of psychoactive compounds have also shown therapeutic values and are prescribed by physicians and other healthcare practitioners.

The active constituents of the majority of psychoactive organisms, such as plants, fungi, animals, or yeasts, fall within a class of basic, naturally occurring, nitrogen-containing, organic compounds known as alkaloids (e.g. nicotine, morphine, cocaine, mescaline, caffeine, ephedrine, psilocin). Alkaloids have a wide range of pharmacological activities including antimalarial, antiasthma, anticancer, cholinomimetic, vasodilatory, antiarrhythmic, analgesic, antibacterial, and antihyperglycemic activities. Many alkaloids have found use in traditional or modern medicine, or as starting points for drug discovery. Recently, psychotropic and stimulant activities of psychoactive alkaloids have been gaining interest from researchers as therapeutic agents for treating various conditions such as alcoholism, opioid addiction and pain to name a few.

Psychoactive alkaloids present in natural sources can be broadly divided into two categories, which are phosphorylated psychoactive alkaloids and dephosphorylated psychoactive alkaloids, although other non-phosphorylatable psychoactive alkaloids may also be present in a natural source. Phosphorylated psychoactive alkaloids are phosphoric acid esters of dephosphorylated psychoactive alkaloids and are biosynthesized in natural sources. Dephosphorylated forms of these psychoactive alkaloids are the bioactive forms that are converted through phosphatase action or chemical hydrolysis. In the human body, upon ingestion, phosphorylated psychoactive alkaloids are dephosphorylated to their corresponding dephosphorylated bioactive forms upon the action of endogenous phosphatase enzymes, which are predominantly found in the gut. For example, to achieve its desired effect, psilocybin must be dephosphorylated to psilocin by a phosphatase enzyme in the gastrointestinal tract.

Oral administration of phosphorylated psychoactive alkaloid compositions via the human gastrointestinal tract allows the conversion of the phosphorylated form to the corresponding biological effective dephosphorylated form. Additionally, the oral route of administration is convenient and ensures patient compliance. However, bioavailability of active pharmaceutical ingredients (APIs) via enteric administration is heavily dependent on an ingredient's ability to be absorbed across the intestinal epithelium and first pass metabolism. Enteric routes of administration also pose challenges such as long onset of action, gastric irritation, etc. Further, the ingestion of dosage forms via the oral route, which involves chewing or swallowing, is problematic for children and geriatric patients.

Often, to overcome these challenges, administration of an API is done via parenteral and topical routes. Delivery of APIs via these routes of administration allows bypassing the first pass metabolism. Furthermore, onset of action of the API is faster than oral ingestion. Dosage forms for administration of psychoactive alkaloids via parenteral routes, such as nasal sprays, inhalers, sublingual absorption, and like have been considered by researchers.

International application PCT/US2020/040826 to Arnold discloses parenteral methods of delivering psilocin and psilocybin, without distinguishing between the two, via parenteral methods.

However, parenteral routes of administration do not facilitate the dephosphorylation of phosphorylated psychoactive alkaloids because they are delivered to an area of the body where little to no dephosphorylation occurs. Thus, often only little to none of the corresponding bioactive dephosphorylated psychoactive alkaloids are delivered to the intended site of action.

Additionally, psychoactive alkaloid extracts are often present in form of a sticky tar, which is difficult to handle or standardize into compositions with specific amounts of psychoactive alkaloids that can be formulated into desired dosage forms.

This background information is provided to reveal information believed by the applicant to be of possible relevance to the present invention. No admission is necessarily intended, nor should be construed, that any of the preceding information constitutes prior art against the present invention.

SUMMARY OF INVENTION

The inventors have realized that there is a need for a non-ingestive psychoactive alkaloid composition capable of providing desired levels of bioactivity in the systemic circulation. In particular, there is need for a non-ingestive psychoactive alkaloid composition that allows for rapid delivery of the psychoactive alkaloid into the systemic circulation, and does not adversely affect the bioavailability of the psychoactive alkaloid, thus allowing the psychoactive alkaloid to achieve the desired psychoactive effects. The psychoactive alkaloid composition is a transdermal composition with a dephosphorylated psychoactive alkaloid, a carrier, a permeation enhancer, a thickening or gelling agent, and optionally one or more further excipients. Use of a dephosphorylated psychoactive alkaloid allows for a non-ingestive delivery mechanism, with its attendant benefits and without the downside of a lack of an available dephosphorylation process within the body. The psychoactive alkaloids may be extracted or synthetic, in either solid or liquid form. The further excipients may include an antioxidant and a bioavailability enhancer.

Disclosed is a transdermal psychoactive alkaloid composition comprising, by weight: 0.1-40% of a psychoactive alkaloid component; 1-30% of alcohol; 1-80% of one or more permeation enhancers; and 1-20% of one or more thickening agents, one or more gelling agents or both one or more thickening agents and one or more gelling agents.

Also disclosed is a process for obtaining a transdermal psychoactive alkaloid composition, the process comprising: extracting psychoactive alkaloid from a dried powdered psychoactive alkaloid source using an acidified solvent with a pH of 3.5 or lower, to obtain a psychoactive alkaloid liquid; adjusting the pH of the psychoactive alkaloid liquid to a pH ranging from 3.5-4.5; evaporating the solvent from the psychoactive alkaloid liquid to obtain a psychoactive alkaloid extract with more dephosphorylated psychoactive alkaloid than phosphorylated psychoactive alkaloid; and mixing the psychoactive alkaloid extract with alcohol, at least one permeation enhancer, and at least one thickening or gelling agent to obtain the transdermal psychoactive alkaloid composition.

This summary does not necessarily describe all features of the invention in detail and is not intended to limit the invention.

BRIEF DESCRIPTION OF DRAWINGS

The following drawings illustrate embodiments of the invention, which should not be construed as restricting the scope of the invention in any way.

FIG. 1 illustrates the steps of a process for obtaining a psychoactive alkaloid extract with dephosphorylation control, according to an embodiment of the present invention.

FIG. 2 illustrates the steps of a process for obtaining a purified psychoactive alkaloid extract according to an embodiment of the present invention.

FIG. 3 illustrates the key steps of a process for obtaining a transdermal psychoactive alkaloid composition, according to an embodiment of the present invention.

DESCRIPTION

A. Glossary

Figure 4:
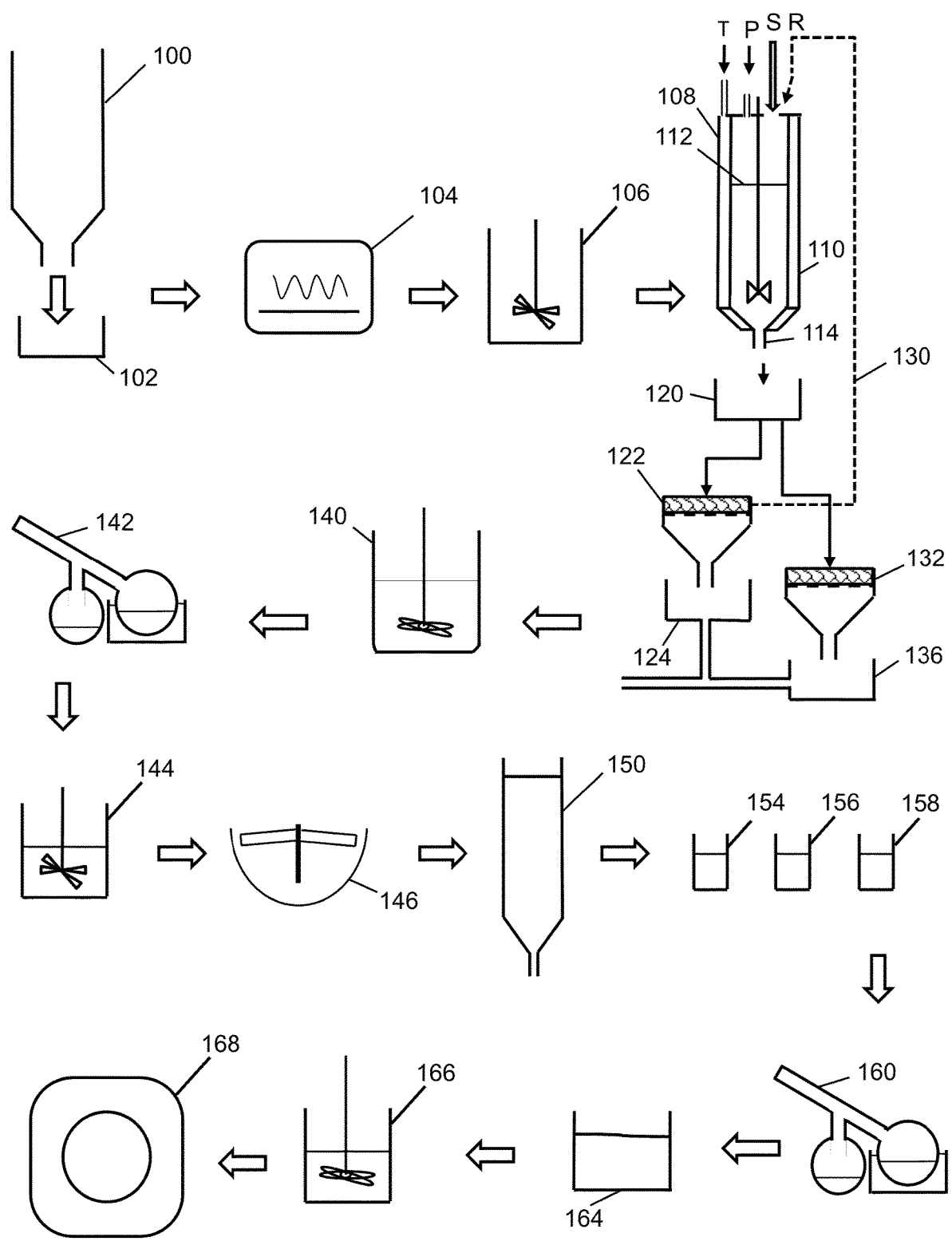
FIG. 4 illustrates a schematic diagram of the apparatus used for obtaining transdermal psychoactive alkaloid compositions according to embodiments of the present invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. Terms such as "alcohol" and "alkaloid" are used as uncountable nouns, unless the context clearly indicates that a specific type of alcohol or alkaloid is being referred to. The terminology herein is used to describe specific embodiments of the invention, but their usage does not delimit the invention, except as outlined in the claims.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. In some embodiments, as the ranges become narrower and more central compared to the greatest range, the properties of the embodiments generally become more balanced, such properties being solubility, viscosity, flowability, stability, potency, immediate potency, delayed potency, cost of production, efficiency of production, production time, compatibility of the psychoactive alkaloid composition, psychoactive efficacy of the psychoactive alkaloid extract, psychoactive efficacy of the psychoactive alkaloid composition, and so on. As the ranges become narrower towards one extreme or other of the widest range, a particular property of the composition or process generally becomes more pronounced relative to the other properties. The specific range is to be chosen depending on how the properties are to be traded-off against each other. As will also be understood by one skilled in the art, all language such as "up to," and the like include the number recited, and any tolerance explicitly or implicitly associated with it, and refer to ranges which can be subsequently broken down into subranges as discussed above. Finally, as will be understood by one skilled in the art, a range includes each individual member.

The term "psychoactive alkaloid" used herein refers to alkaloids that upon ingestion or other bodily intake are capable of changing brain function, for example resulting in alterations in perception, mood, consciousness, cognition, or behavior. The psychoactive alkaloid to which the present invention applies is predominantly a dephosphorylated psychoactive alkaloid, rather than a phosphorylated alkaloid or non-phosphorylatable alkaloid.

The term "psychoactive alkaloid source" used herein refers to an organism such as a fungus, a mycelium, a spore, a plant, a bacterium, an animal or a yeast, which has in it a phosphorylated psychoactive alkaloid, a dephosphorylated psychoactive alkaloid, or a combination or both. The source of the psychoactive alkaloid can also be an extract or a solution with a phosphorylated psychoactive alkaloid, a dephosphorylated psychoactive alkaloid, or a combination of both.

The term "phosphorylatable" refers to psychoactive alkaloids that have phosphorylated derivatives and includes psychoactive alkaloids in both their phosphorylated and dephosphorylated forms.

The term "psychoactive alkaloid composition" used herein can also be referred to as "composition" and describes a mixture of a psychoactive alkaloid possibly with extracted impurities, and one or more excipients. The composition can be of pharmaceutical, nutraceutical, or veterinarian grade.

The term "psychoactive alkaloid liquid" used herein refers to psychoactive alkaloid obtained in liquid form after a dried powdered biomass of a psychoactive alkaloid source has been extracted using an acidified solvent or a basified solvent. The liquid form can be a solution or a slurry.

The term "purified psychoactive alkaloid solution" refers to a solution of one or more desired psychoactive alkaloids, where the solution is free of impurities or contains fewer impurities compared to a similar psychoactive alkaloid solution that has not undergone any purification. The purified solution is obtained after a psychoactive alkaloid extracted from its source has been purified using a resinous material as described herein. Complete or partial evaporation of solvent from the purified psychoactive alkaloid solution results in a purified psychoactive alkaloid extract.

The term "psychoactive alkaloid extract" used herein refers to a psychoactive alkaloid extract obtained by an extraction process described herein or other process. The extract can be in a powdered or a semi-solid or slurry form.

The term "purified psychoactive alkaloid extract" used herein refers to a psychoactive alkaloid extract that has been purified using resinous material as described herein or otherwise. The purified psychoactive alkaloid extract has fewer impurities compared to a similar psychoactive alkaloid extract that has not undergone any purification. The extract can be in a powdered or a semi-solid or slurry form.

As used herein, the expression "standardization of" or "standardizing" the psychoactive alkaloid extract refers to adding a measured amount of one or more excipients to a psychoactive alkaloid extract or synthetic psychoactive alkaloid to achieve a transdermal psychoactive alkaloid composition. Addition of a pre-calculated percentage concentration of non-active pharmaceutical ingredients to the psychoactive alkaloid extract or synthetic psychoactive alkaloid results in standardization of the transdermal psychoactive alkaloid composition. The standardization process ensures that the transdermal psychoactive alkaloid composition has a specific amount of total psychoactive alkaloid content in the composition. This specific amount is accurate up to two or three significant figures. This specific amount is defined as a percentage by weight and can be selected by a person of skill in the art according to preference.

The term "resin" as used herein is intended to refer to a solid or highly viscous substance of plant, mineral, or synthetic origin that has been typically converted into a polymer. Resins are usually mixtures of organic compounds. They are typically used in chromatographic techniques as a stationary phase to purify and separate compounds depending on their polarity. Resins can be physically or chemically modified to provide specificity to bind or repel particular molecules within sometimes very complex mixtures.

As used herein, the term "ion exchange resin" refers to an insoluble organic polymer containing charged groups that attract and hold oppositely charged ions present in a surrounding solution in exchange for counterions previously held. Suitable ion exchange resins to be used herein contain cationic groups that attract and hold anions present in a surrounding solution and are sometimes referred to as "anion ion-exchange resins". Similarly, other ion exchange resins used herein contain anionic groups that attract and hold cations present in a surrounding solution and are sometimes referred to as "cation ion-exchange resins".

The term "macroporous resin" as used herein refers to a nonionic, cation or anion resin with very small, highly cross-linked polymer particles with tiny channels. Macroporous resins are generally used for the adsorption of organic constituents due to their hydrophobic properties and are thus used to separate and purify compounds. The adsorption capacity of macroporous resins not only correlates with the physical and chemical properties of the adsorbent, but also with the size and chemical features of the adsorbed substance.

The term "adsorbed psychoactive alkaloid" refers to one or more alkaloids that are adsorbed onto a resinous material.

The term "purified water" includes deionized water, distilled water, reverse osmosis water, or otherwise purified water which is substantially without free ions.

As used herein, the term "specific amount" when referring to a total psychoactive alkaloid content means a desired percentage, accurate, for example, to one or two decimal places or one, two or three significant figures, of total psychoactive alkaloid content in a psychoactive alkaloid composition or a psychoactive alkaloid extract. The specific amount is defined as a percentage by weight and can be selected by a person of skill in the art according to preference.

The term "specific pH" herein refers to a definite pH value of a solvent or a psychoactive alkaloid liquid obtained by adding an acidified solvent or a basified solvent.

The term "desired amount" herein refers to an amount of a phosphorylated psychoactive alkaloid or a dephosphorylated psychoactive alkaloid in a total psychoactive alkaloid content, in the psychoactive alkaloid liquid, extract or composition. The amount of each of these alkaloids is controlled by the process for making the psychoactive alkaloid extract or psychoactive alkaloid composition. The amounts can be altered by a person of skill in the art according to preference. The amounts are usually percentages by weight that may be accurate up to two or three significant figures.

The "impurities" herein are commonly undesired, but not necessarily harmful, substances encountered while extracting psychoactive alkaloids from a natural source. Impurities may include sugars, carbohydrates, chitin, chitosan, fats, minerals, waxes, and/or proteins. The impurities being removed from a psychoactive alkaloid extract will vary depending on the source of the psychoactive alkaloid. Their removal increases the concentration of the desired psychoactive alkaloids remaining in the extract.

The term "total psychoactive alkaloid content" used herein refers to the total amount of psychoactive alkaloid present in the psychoactive alkaloid composition. The amount is usually a percentage by weight that may be accurate up to two or three significant figures.

The expression "total psychoactive alkaloid content in the psychoactive alkaloid extract" or "total psychoactive alkaloid content by weight of the psychoactive alkaloid extract" used herein refers to amount of a total psychoactive alkaloid content present in a psychoactive alkaloid extract. The amount is usually a percentage by weight that may be accurate up to two significant figures or more.

The term "active pharmaceutical ingredient" or "API" used herein refers to an active ingredient in a pharmaceutical composition or pharmaceutical drug that is biologically active.

The term "non-active pharmaceutical ingredients" used herein refers to non-medical ingredients of a composition which do not have any have any effect on the body. They are generally used to improve stability of a composition's formulation, bulk up formulations, and more. The term as used herein includes a polymer, a carrier, and one or more other excipients.

The term "bioavailability" used herein refers to the fraction of an API that is available in the systemic circulation after administration. This fraction of API in the systemic circulation is therefore available for delivery to the intended site of action.

The term "transdermal" used herein refers to the route of administration in which an active pharmaceutical ingredient is diffused through a skin tissue.

The term "rapid delivery" means initial immediate rapid release and delivery of an API from a composition. The rapid delivery is typically followed by a time-dependent reduction in release of the API from the composition or device and delivery of the drug to the plasma.

The term "excipient" means any component added to an active ingredient to make a composition. An excipient is inert in relation to the active ingredient, in that it essentially does not act in the same way as the active ingredient. An excipient may be completely inert, or it may have some other property that protects the integrity of the active ingredient or assists its uptake into the human body. There are multiple types of excipient, each having a different purpose, and a given excipient may fulfill more than one purpose. Examples of types of excipient include permeation enhancers, mucoadhesive polymers, surfactants, thickening agents, gelling polymers, flowability agents, flavoring agents, sweeteners, colorants, palatants, antioxidants, bioavailability enhancers, viscosity modifying agents, tonicity agents, drug carriers, sustained-release agents, comfort-enhancing agents, emulsifiers, solubilizing aids, lubricants, carriers, binders, disintegrants and stabilizing agents. Specific excipients include pectin, rice husks, rice, xanthum gum, gum arabic, beta cyclodextrin, alpha cyclodextrin, microcrystalline cellulose, sorbitol, dextrose, guar gum, acacia gum, cellulose gum, talc, magnesium stearate.

The term "permeation enhancer" or, equivalently, "penetration enhancer" is an excipient that increases the ability of a drug to pass through human skin, by temporarily increasing the permeability of the skin.

The phrase "one or more excipients" is used herein to refer that one excipient or more than one excipient can be used in any combination. The number of excipients to be used will be at the discretion of a person skilled in the art, and they may be of different types.

The term "thickening agent" refers to an excipient that increases the viscosity of the liquid to which it is added.

The term "gelling agent" refers to an excipient that provides a three-dimensional structure or matrix to the liquid to which it is added.

The term "desired psychoactive effects" herein refers to intended changes in nervous system function resulting in alterations in perception, mood, consciousness, cognition, or behavior that are achieved upon administration of a psychoactive alkaloid composition.

The term "therapeutic" is intended to qualify the amount of active ingredients required in the treatment of a disease or disorder or on the effecting of a clinical endpoint.

Reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

B. Composition

In some embodiments, the present invention relates to a transdermal psychoactive alkaloid composition having a psychoactive alkaloid extract, a permeation enhancer, a carrier, a thickening or gelling agent, and optionally one or more further excipients. In some embodiments, the psychoactive alkaloid extract has a desired amount of a phosphorylated psychoactive alkaloid and a desired amount of a dephosphorylated psychoactive alkaloid. That is, the proportion of dephosphorylated to phosphorylated alkaloids is controlled. In some embodiments, a majority or all of the alkaloids are dephosphorylated. In some embodiments, the psychoactive alkaloid extract additionally includes other psychoactive alkaloids that are not phosphorylatable. In some embodiments, a synthetic psychoactive alkaloid is used instead of the psychoactive alkaloid extract. In some embodiments, the synthetic psychoactive alkaloid has no phosphorylated alkaloid content, or is entirely dephosphorylated psychoactive alkaloid.

The composition is, for example, a hydrogel with an alcohol carrier. Depending on the matrix composition, the application of the gel is modulated by the viscosity and matrix properties. When the composition is a viscous liquid, it can be applied much like an ointment or salve, while a composition that is a thicker hydrogel with more polymer can be applied with an adhesive inert backing, much like a patch.

The transdermal compositions allow the delivery of psychoactive alkaloids into the patient's bloodstream while bypassing the gastrointestinal tract and the hepatic metabolism. As such, they result in a higher bioavailability of the dephosphorylated psychoactive alkaloids to the patient compared to ingested forms, which may suffer degradation en route to the bloodstream. This also allows for lower dosage requirements of psychoactive alkaloids to achieve the desired psychoactive effects.

In some embodiments, the transdermal psychoactive alkaloid composition is formulated as a gel, gel-forming liquid, cream, lotion, ointment, foam, film, hydrogel, capsule, tablet, microparticles, microcapsules, nanoparticles, nanocapsules, spray, solution, emulsion, suspension, paste or the like. Any form of drug dosage form that will effectively deliver the psychoactive alkaloids transdermally into the general blood circulation is intended to be included within the scope of this invention.

The psychoactive alkaloid composition of the present invention can be used, for example, in medical research on the use of psychedelic substances in treatments for mental illnesses.

B1. Psychoactive Component

The psychoactive component is either an extract or synthetic.

The extract may be obtained from any psychoactive organism, such as a plant, fungus or animal, and the extract may be in solid or liquid form, the liquid form being, for example, a slurry or a solution. In some embodiments, the psychoactive component is a psychoactive alkaloid extract that forms 1 to 40% by weight of the composition. In other embodiments, the psychoactive alkaloid extract forms 10% to 20% by weight of the composition.

In some embodiments, the psychoactive alkaloid extract has a total psychoactive alkaloid content ranging from 0.1% to 99% by weight of the extract. In other embodiments, the psychoactive alkaloid extract has a total psychoactive alkaloid content ranging from 1% to 75% by weight of the extract. In yet other embodiments, the psychoactive alkaloid extract has a total psychoactive alkaloid content ranging from 1.03% to 3.02% by weight of the extract. In other embodiments, the psychoactive alkaloid composition has a total psychoactive alkaloid content ranging from 10.00% to 20.00% by weight of the composition. The total psychoactive alkaloid content in the psychoactive alkaloid extract may be defined as a percentage up to two decimal places.

In some embodiments, the psychoactive alkaloid extract further includes naturally occurring substances. The naturally occurring substances are present in the psychoactive alkaloid extract in a concentration ranging from 1% to 99.9% by dry weight. These naturally occurring substances do not normally lead to any side effects or adverse effects when in contact with the skin or when entering the body transdermally as part of the composition. The naturally occurring substances referred to herein include fats, sugars, carbohydrates, chitin, chitosan, minerals, waxes, proteins, or any combination selected therefrom. The concentration range of the naturally occurring substances in the psychoactive alkaloid extract or the purified psychoactive alkaloid extract will vary due to various factors for example, but not limited to, the source of the psychoactive alkaloid extract, the extraction technique used, the efficiency of the extraction process, and the amount of the psychoactive alkaloid in the extract.

The psychoactive component includes predominantly dephosphorylated psychoactive alkaloid in comparison to phosphorylated psychoactive alkaloid. In some embodiments, the desired amount of the dephosphorylated psychoactive alkaloid is over 50% by weight of the total psychoactive alkaloid content in the psychoactive alkaloid extract, and the desired amount of the phosphorylated psychoactive alkaloid is the remainder. In some embodiments, the desired amount of the dephosphorylated psychoactive alkaloid is 100% by weight of the total psychoactive alkaloid content in the psychoactive alkaloid extract. In some embodiments, the desired amount of the dephosphorylated psychoactive alkaloid is 100% by weight of the total phosphorylatable psychoactive alkaloid content in the psychoactive alkaloid extract.

In some embodiments, the psychoactive alkaloid extract is present in its purified form i.e. as a purified psychoactive alkaloid extract. In some embodiments, the purified psychoactive alkaloid extract has a total psychoactive alkaloid content ranging from 10% to 99% by weight of the purified psychoactive alkaloid extract. The naturally occurring substances are present in the purified psychoactive alkaloid extract in a concentration ranging from 1% to 90% by dry weight. In some embodiments, the purified psychoactive alkaloid extract has a total psychoactive alkaloid content ranging from 10.00% to 20.00% by weight of the purified psychoactive alkaloid extract.

In some embodiments, the desired amount of the dephosphorylated psychoactive alkaloid is over 50% by weight of the total psychoactive alkaloid content in the purified psychoactive alkaloid extract, and the desired amount of the phosphorylated psychoactive alkaloid is the remainder. In some embodiments, the desired amount of the dephosphorylated psychoactive alkaloid is 100% by weight of the total psychoactive alkaloid content in the purified psychoactive alkaloid extract. In some embodiments, the desired amount of the dephosphorylated psychoactive alkaloid is 100% by weight of the total phosphorylatable psychoactive alkaloid content in the purified psychoactive alkaloid extract.

The composition of the present invention has a total psychoactive alkaloid content present in a specific amount. In some embodiments, the specific amount of the total psychoactive alkaloid content is accurate to one significant figure. In other embodiments, the specific amount of the total psychoactive alkaloid content is accurate to two, three or four significant figures. The presence of the total psychoactive alkaloid content in a specific amount in the composition is possible despite the variation of psychoactive content in different batches of the extract, because the content in each batch is known and the amount of each extract used can be chosen accordingly.

In some embodiments, the phosphorylated alkaloid is psilocybin, baeocystin, norbaeocystin, aeruginascin, an alkaloid with similar properties, or any combination therefrom; and the dephosphorylated alkaloid is psilocin, bufotenine, bufotenidine, norpsilocin, 4-hydroxytryptamine (4-HT), N,N,N-trimethyl-4-hydroxytryptamine, 4-hydroxy-N,N,N-trimethyltryptamine (4-HO-TMT), an alkaloid with similar properties, or any combination therefrom.

In some embodiments, the psychoactive component is a synthetic psychoactive alkaloid component. In some embodiments, the synthetic psychoactive alkaloid component has a psychoactive alkaloid content of up to 99%, and the amount of the synthetic psychoactive alkaloid component is 0.1-30% by weight of the composition. In some embodiments, the amount of synthetic psychoactive alkaloid component is 0.1-10% by weight of the composition. The psychoactive alkaloid in the synthetic psychoactive alkaloid component may be entirely dephosphorylated psychoactive alkaloid, for example psilocin. In other embodiments, the psychoactive alkaloid in the synthetic psychoactive alkaloid component may be partly dephosphorylated psychoactive alkaloid, for example psilocin and partly phosphorylated, for example psilocybin.

B2. Carrier

The carrier is a C1-C4 alcohol, individually chosen from or is a mixture of ethanol, 1-propanol, isopropyl alcohol and tert-butyl alcohol. In some embodiments, the carrier forms 1-30% by weight of the composition. In some embodiments, the carrier forms 10-20% by weight of the composition.

B3. Permeation Enhancer

In some embodiments, the permeation enhancer (penetration enhancer) forms 1-80% by weight of the composition. In other embodiments, the permeation enhancer forms 15-40% by weight of the composition. This latter range is given because enhancers increase their permeation of the skin at higher concentrations and it is desirable to have as much permeation enhancer as possible, but not so much that the composition begins to separate out while in storage, or becomes unstable in relation to the gel matrix or active ingredient.

In other embodiments, there are two different permeation enhancers: a first permeation enhancer and a second permeation enhancer together forming 1-80% by weight of the composition. In other embodiments, the two different permeation enhancers together form 15-40% by weight of the composition. The benefit of having two different permeation enhancers is that the penetration properties are modulated. By combining two permeation enhancers, they form a more heterogeneous matrix in which the active ingredient is entrained. In other embodiments, more than two different permeation enhancers may be present in the composition.

Due to the skin-penetrating properties of the psychoactive alkaloid composition upon contact with the skin, due to the presence of the permeation enhancer, percutaneous delivery of the psychoactive alkaloid is facilitated. Examples of the permeation enhancer include agarose, chitosan, gelatin, hyaluronic acid, guar gum, hakea gum, xanthan gum, gellan gum, carragenan gum, pectin gum, and sodium alginate, CMC (carboxymethylcellulose), thiolated CMC, sodium CMC, HEC (hydroxyethylcellulose), HPC (hydroxypropyl cellulose), HPMC (hydroxypropyl methyl cellulose), MC (methyl cellulose), MHEC (methyl hydroxyethyl cellulose), poly(acrylic acid)-based polymers, carbomers, PAA, polyacrylates, poly(methylvinylether-co-methacrylic acid), poly (2-hydroxyethyl methacrylate), poly(acrylic acid-co-ethylhexylacrylate), poly(methacrylate), poly (alkylcyanoacrylate), poly(isohexylcyanoacrylate), poly (isobutylcyanoacrylate), copolymer of acrylic acid, PEG (polyethylene glycol), poloxamers, poly(N-2-hydroxypropyl methacrylamide) (PHPMAm), polyoxyethylene, PVA (Polyvinylalcohol), PVP (polyvinylpyrrolidone), thiolated polymers, sodium tauroglycocholate, propylene glycol, isopropyl myristate, and diethylene glycol monoethyl ether, ethyl acetate, oleyl acetate, propylene glycol monocaprylate, octyl salicylate, lauric acid, linoleic acid, oleic acid, palmitic acid, isostearic acid, propylene glycol, dipropylene glycol, 1,2-butylene glycol, N-methyl-2-pyrrolidones, 2-pyrrolidone, dimethyl sulphoxide, decylmethyl sulphoxide, cineole, eugenol, D-limonene, linalool, menthol, menthone, phosphatidylcholine (PC), hydrogenated phosphatidylcholine, phosphatidic acid (PA), phosphatidylserine (PS), phosphatidylethanolamine (PE), phosphatidylglycerol (PPG), phosphatidylinositol (PL) and water.

B4. Thickening or Gelling Agent

The composition includes a thickening agent or gelling agent, which acts to increase the viscosity of the composition so that it does not easily run off the skin. Where a gelling agent is used, a structural matrix is formed in the composition. In some embodiments, the thickening or gelling agent is present in the composition in a concentration ranging from 1-20% by weight of the composition. In general, below 1%, the thickening agent or gelling agent will have little effect, and above 20%, the composition as a cream will become too viscous or the gel too hard. In other embodiments, the thickening or gelling agent is present in the composition in a concentration ranging from 5-10% by weight of the composition.

The thickening or gelling agent is individually chosen from or is a mixture of polyacrylic acid; hydroxypropyl cellulose, hydroxyethylcellulose or other cellulosic ethers; other polymeric thickening agents such as xanthan gum, guar gum, and the like, fatty alcohols, fatty acids and their alkali salts and mixtures thereof, as well as inorganic thickeners/gelling agents.

B5. Antioxidant

Optionally, in some embodiments, the composition includes an antioxidant. In some embodiments, the antioxidant is present in the composition in a concentration ranging from 1-5% by weight of the composition. In other embodiments, the antioxidant is present in the composition in a concentration ranging from 3-5% by weight of the composition. The antioxidant provides chemical stability to the composition so that it has a longer shelf life compared to compositions without the antioxidant. The amount of antioxidant should be added in sufficient quantity to provide stability to the composition, without adding so much that it deleteriously affects the matrix of the gel or the viscosity.

In some embodiments, the antioxidant is individually chosen from or is a mixture of benzyl alcohol, ascorbic acid, methylparaben, propylparaben, benzalkonium chloride, thiomersal, sodium bisulfite, sodium meta bisulfite or thiourea.

B6. Bioavailability Enhancer

Optionally, in some embodiments, the composition includes a bioavailability enhancer. Bioavailability enhancers bind to active pharmaceutical ingredients and either increase their stability, ability to cross membranes, or prevent the body from breaking down the API. In one embodiment, the bioavailability enhancer is present in the composition in a concentration ranging up to 5% by weight of the composition. In another embodiment, the bioavailability enhancer is present in the composition in a concentration ranging from 0.5-2% by weight of the composition. Utilization of bioavailability enhancers in these relatively small concentrations decreases the occurrence of an adverse effect, and only small concentrations are needed to be effective. Examples of bioavailability enhancer include, but are not limited to, beta cyclodextrin, alpha cyclodextrin, piperine, citric acid, and beta-carbolines (MAOI) such as harmaline.

C. Extraction with Dephosphorylation Control

In one embodiment, referring to FIG. 1, a process for obtaining a psychoactive alkaloid extract with dephosphorylation control, according to an embodiment of the present invention is shown. Dephosphorylation applies to the psychoactive alkaloids that are phosphorylatable.

The process includes step 10 of obtaining powdered biomass from a psychoactive alkaloid source, such as a psychoactive organism. The powdered biomass is obtained by drying and pulverizing the psychoactive alkaloid source. The drying is carried out via vacuum desiccation, freeze drying, timed forced air drying, or other suitable drying method known to a person of skill in the art, to obtain a dried biomass. The pulverization is carried out by milling, grinding, or other method to reduce the particle size of the dried biomass.

In one embodiment, the drying is carried out in a forced air oven completely shielded from all light at 20-30° C. for a time period of 5-10 hours. However, there is room for optimization of the drying step, using different temperatures (e.g. 10-50° C.) and different durations.

In one embodiment, the psychoactive alkaloid source is a mushroom from the genus *Conocybe, Copelandia, Galerina, Gymnopilus, Inocybe, Panaeolus, Pholiotina, Pluteus* or *Psilocybe*, or any combination of mushrooms selected therefrom. In one embodiment, gills, caps, stems, or the whole of the fungi is used as the alkaloid source. In other embodiments, the psychoactive alkaloid source is another organism, such as another fungus, a plant or an animal.

Step 12 involves extracting the psychoactive alkaloid from the dried powdered biomass with an acidified solvent or a basified solvent to obtain a psychoactive alkaloid liquid with a specific pH, wherein the specific pH is lower than 3.5 or over 10.5.

When used, the acid in step 12 may be acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate monobasic, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination of one or more of these. In some embodiments, the acid is either only hydrochloric acid or only phosphoric acid, for example. It is also envisaged that other acids may be used, for example non-food-grade acids that may be used by pharmaceuticals.

When used, the base in step 12 may be ammonium bicarbonate, ammonium carbonate, ammonium hydroxide, calcium acetate, calcium carbonate, calcium chloride, calcium hydroxide, calcium lactate, calcium oxide, calcium phosphate dibasic, calcium phosphate monobasic, magnesium carbonate, potassium aluminum sulphate, potassium bicarbonate, potassium carbonate, potassium hydroxide, potassium lactate, potassium phosphate dibasic, potassium pyrophosphate tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic or any combination therefrom. In one embodiment, the base is solely sodium hydroxide, for example. Other bases may be used in other embodiments, for example non-food-grade bases that may be used by pharmaceuticals.

In some embodiments, the acidified solvent is a mixture of an acid and a C1-C4 primary aliphatic alcohol, a C3-C4 ketone, water, or any combination selected therefrom. The acid may be citric acid, ascorbic acid, formic acid, acetic acid, hydrochloric acid, phosphoric acid, sulphuric acid, or any combination selected therefrom. In other embodiments, the basified solvent is a mixture of a base and a C1-C4 primary aliphatic alcohol, a C3-C4 ketone, water, or any combination selected therefrom. The base may be sodium hydroxide, potassium hydroxide, ammonium hydroxide, sodium bicarbonate, calcium carbonate, or any combination selected therefrom.

After adding the acidified solvent, if the acidified solvent used, the psychoactive alkaloid liquid has a pH ranging from 0.5-3.5. In an exemplary embodiment, the pH of the psychoactive alkaloid liquid obtained after addition of the acidified solvent is 2. The pH is adjusted to lower than 3.5 in the extraction step 12 to promote the conversion of phosphorylated psychoactive alkaloid to dephosphorylated psychoactive alkaloid, thus allowing the preparation of the psychoactive alkaloid liquid with the predominantly or entirely dephosphorylated psychoactive alkaloid. For example, with pH conditions lower than 3.5, psilocybin is readily converted to psilocin. In some embodiments, during the extraction step the psychoactive alkaloid liquid has a pH lower than 3.5 and the desired amount of the phosphorylated psychoactive alkaloid is 0% by weight of the total psychoactive alkaloid content in the psychoactive alkaloid extract. The desired amount of the dephosphorylated psychoactive alkaloid is 100% by weight of the total psychoactive alkaloid content in the psychoactive alkaloid extract. Even with neutral hydroethanol extraction, a large portion of psilocybin may be converted to psilocin. However, the low pH environment (<3.5) protects the psilocin from oxidation.

If the pH in step 12 were 10.5 or higher, then the conversion of phosphorylated alkaloids to dephosphorylated alkaloids would be inhibited, and the result would be predominantly or entirely phosphorylated alkaloids. This may be limited by the initial amount of alkaloids in the psychoactive alkaloid source that were already dephosphorylated. As predominantly dephosphorylated alkaloids are more useful in the present composition than phosphorylated alkaloids, then the acidified solvent would be chosen in step 12.

In some embodiments, the extraction is performed at a temperature ranging from 5-95° C. In other embodiments, the extraction is performed at a temperature ranging from 50-75° C. In other embodiments, the extraction is performed at room temperature.

In some embodiments, the extraction is performed for a time period ranging from 10-720 minutes. For most cases, a time below 10 min would result in a mostly incomplete yield, and above 720 min the extraction may be incomplete but would be continuing at a negligible rate. In another embodiment, and more usually, the extraction is performed for a time period ranging from 30-240 minutes.

In some embodiments, the extraction is performed at a pressure ranging from 7 to 20,000 psi. In yet another embodiment, the extraction is performed at a pressure ranging from 10 to 20 psi. Application of pressure may be used to increase the rate of extraction.

In some embodiments, the extraction is performed with a solvent to solid ratio in the range 1 L:1 kg to 50 L:1 kg, wherein the solid is the dried powdered biomass. In one embodiment, the extraction is performed with a solvent to solid ratio of 20 L:1 kg.

After the addition of the acidified solvent or the basified solvent, the powered biomass and the solvent may be mixed, continually or intermittently, followed by step 14 of filtration to result in an extracted filtrate (i.e. psychoactive alkaloid liquid).

In step 18 of the process, the pH of the obtained psychoactive alkaloid liquid is adjusted to a pH ranging from 3.5-4.5. The pH is adjusted by adding a base or an acid. The pH is adjusted to a value in this range as the psychoactive alkaloid liquid exhibits a good anti-microbial stability in this pH range. Also, there is no conversion (or further conversion, as the case may be) of phosphorylated alkaloids to dephosphorylated alkaloids at this pH after the alkaloids are removed from the biomass, which points to enzymatic hydrolysis being responsible for conversion in the source of the psychoactive alkaloids. In exemplary embodiments, the base is sodium hydroxide and the acid is citric acid. Any other appropriate acid or base can be used to adjust the pH, which a person of skill in the art may determine. The selection of the acid or the base will depend upon the nature of the pH of the psychoactive alkaloid liquid prior to adjusting it to the range of 3.5-4.5.

In some embodiments, the extraction includes further extracting the psychoactive alkaloid by repeating the extraction step. Filtrate residue from step 14 is collected and to this filtrate residue, the same or a different acidified solvent, or the same or a different basified solvent is added, as in step 12. The resulting mixture is mixed and followed by filtration to obtain another filtrate. This filtrate and the previous filtrate are mixed together to result in a bulk or pooled filtrate. To this bulk filtrate the acid or the base is added to adjust the pH to 3.5-4.5 according to step 18. In some embodiments, the further extraction of the filtrate obtained after extraction with the acidified or the basified solvent is repeated until a required amount of the phosphorylated psychoactive alkaloid and/or the dephosphorylated psychoactive alkaloid is extracted. The number of extraction cycles to be repeated will depend on various variable factors such as the source of the psychoactive alkaloid and the solubility of the psychoactive alkaloid in the acidified or the basified solvent.

Step 20 of the process involves evaporating the solvent from the psychoactive alkaloid liquid to obtain the psychoactive alkaloid extract with the desired amount of the phosphorylated psychoactive alkaloid and the desired amount of the dephosphorylated psychoactive alkaloid. The solvent is completely or partially evaporated to result in the psychoactive alkaloid extract as a slurry or powder. The evaporation is carried out by methods such as air-drying, rotary evaporation, or other methods known in the art to suitably evaporate solvent from psychoactive alkaloid liquid. At this point in time, away from the biomass, dephosphorylated/phosphorylated alkaloids are fairly heat resistant, more so under vacuum, and so rotary evaporation, for example, is a suitable process.

Evaporation step 20 may be paused, for standardization in step 21, and continued after standardization. The evaporation of a portion of the solvent, before collection of the psychoactive alkaloid extract, in slurry form, for standardization, is done to obtain a quantity of a psychoactive alkaloid extract slurry that is easy to handle in the subsequent steps of the standardization process. The quantity of the portion of the solvent to be evaporated before pausing the evaporation is not so much as to make it too viscous to handle well. The quantity of the portion of the solvent to be evaporated will depend on various factors, for example, but not limited to, the contents of the psychoactive alkaloid liquid and the quantity of the psychoactive alkaloid liquid present at the beginning of the evaporation step.

For the purposes of the composition disclosed herein, the desired amount of the dephosphorylated psychoactive alkaloid is 100% of the total phosphorylatable psychoactive alkaloid content in the psychoactive alkaloid extract, and the desired amount of the phosphorylated psychoactive alkaloid is 0%. As such, an acidified solvent is selected in step 12. However, it is conceivable that a transdermal composition with 100% or predominantly phosphorylated psychoactive alkaloids may be made for the purposes of study or other uses, in which case a basified solvent is chosen in step 12.

D. Purification

In one embodiment, referring to FIG. 2, steps of a process for obtaining a purified psychoactive alkaloid extract are shown. The main steps are: adsorbing, in step 34, the psychoactive alkaloid extract obtained in step 18 or 20 onto a resin to obtain an adsorbed psychoactive alkaloid, which may include one or more adsorbed psychoactive alkaloids; eluting, in step 38, the adsorbed psychoactive alkaloid using a solvent to obtain a purified psychoactive alkaloid solution; and evaporating, in step 42, the solvent from the purified psychoactive alkaloid solution.

In one embodiment, the psychoactive alkaloid extract obtained in step 18 or is followed by completely or partially concentrating the obtained psychoactive alkaloid extract by evaporation of the solvent from the extract in step 22. If the solvent from the extract has been completely evaporated in step 22, then reverse osmosis water, more solvent or another solvent is added back. Other water may be used in place of reverse osmosis water, which is usually selected for its purity.

In some embodiments, the process includes adding, in step 26, an acid or a base to the psychoactive alkaloid extract obtained in step 20 to obtain a psychoactive alkaloid solution with a desired pH.

When used, the acid may be acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate monobasic, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination of one or more of these. In some embodiments, the acid is either only hydrochloric acid or only phosphoric acid, for example. It is also envisaged that other acids may be used.

When used, the base may be ammonium bicarbonate, ammonium carbonate, ammonium hydroxide, calcium acetate, calcium carbonate, calcium chloride, calcium hydroxide, calcium lactate, calcium oxide, calcium phosphate dibasic, calcium phosphate monobasic, magnesium carbonate, potassium aluminum sulphate, potassium bicarbonate, potassium carbonate, potassium hydroxide, potassium lactate, potassium phosphate dibasic, potassium pyrophosphate tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic or any combination therefrom. In one embodiment, the base is solely sodium hydroxide, for example. Other bases may be used in other embodiments.

In some embodiments, the desired pH psychoactive alkaloid solution has a pH ranging from 2.5-4.5, or from 9-10. In other embodiments, the desired pH psychoactive alkaloid solution has a pH of 3, 4, or 9.5. A person of skill in the art will appreciate that the selection of the pH is chosen in a manner to allow for the efficient adsorption of the psychoactive alkaloids onto the resin(s).

In one embodiment, the process includes adding phosphoric acid to the psychoactive alkaloid extract to achieve a pH of 4. In another embodiment, the process includes adding hydrochloric acid to the psychoactive alkaloid extract to achieve a pH of 3. In yet another embodiment, the process includes adding sodium hydroxide to the psychoactive alkaloid extract to achieve a pH of 9.5.

The process includes, in step 30, optionally filtering, centrifuging, or clarifying the psychoactive alkaloid solution or desired pH psychoactive alkaloid solution, as the case may be, and utilizing the obtained filtrate for the following step of adsorption. Clarifying may be performed, for example, by adding an agglomeration agent. In step 34, the process involves adsorbing the psychoactive alkaloid(s) in the solution onto the resin to obtain an adsorbed psychoactive alkaloid. This may be done, for example, by contacting the psychoactive alkaloid solution with the resin or otherwise treating the psychoactive alkaloid solution with the resin.

In some embodiments, the resin used in step 34 is an adsorbent resin of the macroporous type, such as, a cation or anion ion-exchange resin, a non-ionic resin, or any combination therefrom. Representative pharmaceutical, nutraceutical or food-grade grade resins for use in accordance with the present invention are known to those skilled in the art. For example, pharmaceutical grade non-ionic macroporous resins are commercially available, e.g. Amberlite® XAD4. In some embodiments, the resin is a cationic ion-exchange resin or an anionic-exchange resin. The cationic ion-exchange resin may be selected from commercially available cationic ion-exchange resins known in the art, including but not limited to Amberlite® MAC-3 H. The cationic ion-exchange resin may be in an $H^+$ form or an $Na^+$ form. The anionic ion-exchange resin may be selected from commercially available anion exchange resins known in the art, including but not limited to Amberchrom® 50WX8. The anionic ion-exchange resin may be in an $OH^-$ form or a $Cl^-$ form. The resins used may be of any particle size. In some embodiments, the resins may be gel type resins, with any size of gel bead.

In step 36, the process involves washing the resin to remove adsorbed impurities from the resin. While not all the impurities are adsorbed onto the resin, some of them may be. The washing step, substantially, does not remove the adsorbed psychoactive alkaloids. The washing solvent may be 100% ethanol, 100% reverse osmosis water, or any other washing solvent used in ion-exchange resin chromatography, provided that the washing removes impurities or by-products that are adsorbed on the resin. Impurities or by-products may include, for example, sugars, carbohydrates, chitin, chitosan, fats, minerals, waxes, or proteins. There may be one, two or more washing steps depending on the embodiment, and the same or different washing solvents may be used for each wash. In other embodiments, the solvent(s) for washing may include a primary aliphatic alcohol, a ketone, water, and any combination therefrom. In one embodiment, the primary aliphatic alcohol is a C1-4 alcohol. In one embodiment, the primary aliphatic alcohol is 5% ethanol. In one embodiment, the primary aliphatic alcohol is ethanol. In one embodiment, the ketone is a C3-4 ketone. In yet another embodiment, the water is selected from deionized, distilled, reverse osmosis, or otherwise purified water that is substantially without free ions.

After the washing, the process involves eluting, in step 38, the adsorbed psychoactive alkaloid from the resin using a solvent to obtain a purified psychoactive alkaloid solution. The solvent may be an organic solvent, an acid, a base, or water, a combination of an organic solvent and a base, or a combination of an organic solvent and an acid, a combination of an organic solvent and water, a combination of water and a base, or combination of water and an acid. The result of the elution step is a purified psychoactive alkaloid solution. Usually, the solvent is different from the solvent in which the extract is initially provided, and is either a different type of solvent or a different composition of solvent. It may be at a different temperature than the initial solvent.

In some embodiments, the solvent used in the elution step 38 may be a primary aliphatic alcohol, a ketone, water, and any combination therefrom. In one embodiment, the primary aliphatic alcohol is a C1-4 alcohol. In one embodiment, the primary aliphatic alcohol is 5% ethanol. In one embodiment, the primary aliphatic alcohol is ethanol. In one embodiment, the ketone is a C3-4 ketone. In yet another embodiment, the water is deionized, distilled, reverse osmosis, or otherwise purified water, which is substantially without free ions. In other embodiments, the water is not purified.

In one embodiment, the solvent used in the elution step 38 is a combination of an organic solvent and an acid. In one embodiment, the combination of an acid and an organic solvent is 2% hydrochloric acid and 80% ethanol, for example. In general, any acidic environment will displace some of the ions from the resin, but the rate and optimization of desorption will be affected by the acid concentration. In one embodiment, the solvent used in the elution step 38 is a combination of an organic solvent and a base. In one embodiment, the combination of an organic solvent and a base is of 2% sodium chloride and 80% ethanol, for example. In general, any basic environment will displace some of the ions from the resin, but the rate and optimization of desorption will be affected by the concentration of the base.

All the above solvents and combinations thereof are suitable for the elution step because all of the psychoactive alkaloids of interest are soluble therein and, depending on the choice of resin, they are all capable of pulling the alkaloids of interest off a resin. There are many different resins available, and it is a straightforward matter to select a suitable resin and elution solvent pair.

In one embodiment, the elution step is carried out at a temperature in the range of 4-75° C. These temperatures are limited by the boiling point of the solvent used, as well as the specifications of allowable food-grade resins, as determined by the manufacturers of the resins and governmental food and drug administrations. In another embodiment, the elution step is carried out at room temperature for convenience, i.e. at 21-25° C.

Optionally, the purified psychoactive alkaloid solution obtained after elution is further purified by filtering, in step 39, the obtained purified psychoactive alkaloid solution to obtain a filtrate, and then repeating at least steps 34 and 38 with the obtained filtrate. Steps 34 and 38 can be repeated with the same or a different resinous material and the same or a different solvent to obtain a further or twice-purified psychoactive alkaloid solution.

The result of the elution is a purified psychoactive alkaloid solution. In one embodiment, the purified psychoactive alkaloid solution has a concentration of 0.07% by weight of a psychoactive alkaloid, which is the concentration before removal of some or all of the solvent. This concentration may be different in other embodiments, depending on the amount solvent used for the elution and the potency of the raw materials. In one embodiment, the purified psychoactive alkaloid solution is concentrated by evaporating the solvent to form a purified psychoactive slurry that has at least of 5% by weight or more of psychoactive alkaloid. In another embodiment, the resulting purified psychoactive alkaloid slurry has 5-68% by weight of psychoactive alkaloid. In yet other embodiments, the purified psychoactive alkaloid slurry has a concentration of psychoactive alkaloid outside these ranges, and, when dried, can be as low as 0.1% or as high as 99% dry wt/wt %.

Following the elution, a further washing step 40 may be employed using 100% ethanol, for example, to wash the resin. This may be considered to be a cleaning step, to refresh the resin and make it ready to be used again in a subsequent step or in another process. In other embodiments, the solvent for further washing may be a primary aliphatic alcohol, a ketone, water, and any combination therefrom. In one embodiment, the primary aliphatic alcohol is a C1-4 alcohol. In one embodiment, the primary aliphatic alcohol is 5% ethanol. In one embodiment, the ketone is a C3-4 ketone. In yet another embodiment, the water is selected from deionized, distilled, reverse osmosis, or otherwise purified water that is substantially without free ions.

After elution step 38, the obtained purified psychoactive alkaloid solution undergoes the evaporation step 42 to complete or partially evaporate the solvents and result in the purified psychoactive alkaloid extract (slurry or powder form).

Step 42 involves evaporating the solvent from the purified psychoactive alkaloid solution to obtain the purified psychoactive alkaloid extract with, if dephosphorylation control has been used, the desired amount of the phosphorylated psychoactive alkaloid and the desired amount of the dephosphorylated psychoactive alkaloid (for example, 0% and 100% respectively for the composition herein). The solvent is completely or partially evaporated to result in the psychoactive alkaloid extract (slurry or powder respectively). The evaporation is carried out by methods such as air-drying, rotary evaporation, or other methods known in the art to suitably evaporate solvent from psychoactive alkaloid liquid.

Evaporation in step 42 may be paused, for standardization in step 43, and continued after standardization. The evaporation of a portion of the solvent, before collection of the purified psychoactive alkaloid slurry for standardization, is done to obtain a quantity of a psychoactive alkaloid slurry that is easy to handle in the subsequent steps of the standardization process. The quantity of the portion of the solvent to be evaporated before pausing the evaporation is not so much as to make it too viscous to handle well. The quantity of the portion of the solvent to be evaporated will depend on various factors, for example, but not limited to, the contents of the psychoactive alkaloid solution and the quantity of the psychoactive alkaloid solution present at the beginning of the evaporation step.

E. Standardization

Standardization may be carried out part way through evaporation step 20 (FIG. 1) or evaporation step 42 (FIG. 2), or it may be done after either of these steps. Standardization is more conveniently done when the extract is a slurry than a powder, but it is not necessary that it is a slurry. Firstly, for example for a slurry, the weight percentage of the psychoactive alkaloids in the psychoactive alkaloid extract and the weight proportion of solids in the psychoactive alkaloid extract are measured. The psychoactive alkaloid content in the final composition is specified. A measured amount of one or more excipients is added to the psychoactive alkaloid extract, such that, when the remaining solvent is evaporated, the resultant solid will have the specified content of psychoactive alkaloids. The specific amount of the total psychoactive alkaloid content in the standardized extract may be accurate to one or two decimal places, or one or two significant figures depending on how accurately the measurements are made during the mixing of the psychoactive alkaloid extract and the one or more excipients. The excipients used in standardizing the extract may be, for example, one or more of the excipients that are required in the final transdermal composition, such as a permeation enhancer or an antioxidant.

Standardization results in an standardized, extracted psychoactive alkaloid composition or a standardized psychoactive alkaloid extract. The psychoactive alkaloid extract obtained has a specific amount of total psychoactive alkaloid content. Further, the psychoactive alkaloid is made up of a psychoactive alkaloid with a controlled amount of dephosphorylation, and possibly other psychoactive alkaloids that are not dephosphorylatable.

In other embodiments, the standardization process occurs at the time of preparation of the transdermal composition, in FIG. 3. This is done by selecting the quantities of excipients and psychoactive component so that the final, transdermal composition has the specified concentration of psychoactive alkaloids.

F. Preparation of Composition

In some embodiments, referring to FIG. 3, the key steps of a process for forming a transdermal psychoactive alkaloid composition are shown.

Step 44 involves mixing the carrier (e.g. alcohol, water or a combination of alcohol and water) with one or more permeation enhancers until the mixture is homogenous. After this, the standardized psychoactive component (i.e. the extract, purified extract or synthetic alkaloid) and the antioxidant, if used, are added to the homogenous mixture in step 46. Optionally one or more other excipients may be added to the mixture in step 46, such as a bioavailability enhancer. Again, mixing continues until homogeneity is obtained. A person of skill in the art will appreciate that the mixing steps can be performed by any suitable methods, which do not cause any damage to the active pharmaceutical ingredients or the excipients, as known in the literature.

Following this, in step 48, the thickening agent is added to the mixture. Care should be taken to add the thickening agent slowly and stepwise in order to produce a homogeneous gel.

Finally, the mixture is ready to be packaged and stored, in step 50. In some embodiments, the mixture will be left to dry before packaging, in order to form a harder gel. The packaging process may involve applying the harder gel form of the composition to inactive backing that has an adhesive layer for sticking the backing layer to the skin.

F. Examples

In order to further illustrate the present invention, the following specific examples are given with the understanding that these examples are intended only to be illustrations without serving as a limitation on the scope of the present invention. All parameters, dimensions, materials, quantities and configurations described herein are examples only and may be changed depending on the specific embodiment.

Accordingly, the scope of the invention is to be construed in accordance with the substance defined by the appended claims. The process may be scaled up using larger quantities and modified apparatus.

Although the examples of the present invention have been formulated specifically using *Psilocybe cubensis* as a source to obtain a psychoactive alkaloid extract, the extract comprising predominantly dephosphorylated psychoactive alkaloid (e.g. psilocin), other sources are possible. A person skilled in the art would appreciate that the *Psilocybe cubensis* can be readily substituted by other sources of psychoactive alkaloids to obtain a variety of psychoactive alkaloids having similar properties, such psilocybin, baeocystin, norbaeocystin, aeruginascin, psilocin, norpsilocin, 4-hydroxytryptamine, N,N,N-trimethyl-4-hydroxytryptamine, or any combination therefrom, to name a few, to result in compositions with similar efficacy and efficiency as well. For example, mushrooms from the genus *Conocybe, Copelandia, Galerina, Gymnopilus, Inocybe, Panaeolus, Pholiotina, Pluteus, Psilocybe*, or any combination therefrom may be used.

Example 1: Extraction Process with Promotion of Dephosphorylation 2.5 kilograms of *Psilocybe cubensis* were dried in a forced air oven at 25° C. for 10 hours to result in 140 grams of dried biomass. The dried biomass was then pulverized to a size of 200 mesh with a hammer mill.

An acidified solvent, i.e. a pH-adjusted, hydro-ethanol mixture, was prepared. 144 g of anhydrous citric acid was placed into a 5 L vessel with 1.25 L of reverse osmosis water, followed by the addition of 3.75 L of ethanol. The contents were mixed until completely dissolved. An acidified solvent with a pH of 2 was obtained.

The dried powdered biomass was placed into an agitated, heat-controlled vessel with 5 L of the acidified solvent and mixed for the extraction of psychoactive alkaloid. The extraction was controlled to a constant 75° C., and the duration of extraction was 1 hour. The extraction slurry was then filtered. Filtration resulted in a filtrate, i.e. the psychoactive alkaloid liquid, and a filter residue. The filter residue was placed back into the extraction vessel and extracted with an additional 5 L of the acidified solvent. The temperature of extraction was again 75° C. and the time was 1 hour. The extraction slurry was filtered. The filtrates from the first and second extraction were mixed to form 10 L of mixed filtrate. The pH of the mixed filtrate was then increased with 5 M sodium hydroxide until a pH of 4.5 was achieved. Immediately after adjusting the pH, the mixed filtrate was placed into a rotary evaporator at 50° C. and 250 torr, and the solvent was partially or completely evaporated to obtain a psychoactive alkaloid extract. Final stages of evaporation were performed using a freeze dryer and the psychoactive alkaloid extract was obtained. When dried to a powder, the psychoactive alkaloid extract had a total psychoactive alkaloid concentration of 0.86% by weight of the psychoactive alkaloid extract. Further, the desired amount of the phosphorylated psychoactive alkaloid obtained was 0.00% by weight of the total psychoactive alkaloid content in the psychoactive alkaloid extract. The desired amount of the dephosphorylated psychoactive alkaloid obtained was 100% by weight of the total psychoactive alkaloid content in the psychoactive alkaloid extract.

Example 2.1: Purification with a Non-Ionic Macroporous Resin

The pH of the psychoactive alkaloid extract of example 1, in aqueous form, was adjusted to pH 4.0 (+/−0.5) by adding 2 M phosphoric acid and centrifuged for 15 minutes at 3000 g to remove any solid precipitate. The pH of 4 corresponds to the isoelectric point of psilocybin, and psilocin's polarity is such that it is partitioned onto the resin, thus allowing effective binding of the psychoactive alkaloids psilocybin (if present, i.e. dephosphorylation is not used or is incomplete) and psilocin to the macroporous resin. Norbaeocystin and baeocystin are phosphorylated and would behave in the same way as psilocybin. The supernatant obtained was loaded onto a column of Amberlite® XAD4, a non-ionic macroporous resin (50.34 g of dry resin) at a flow rate of 2 bed volumes per hour, to allow components in the supernatant to be adsorbed onto the macroporous resin. After all 2.5 L of the extract was loaded onto the column of macroporous resin, the column was washed in a single pass with 5 bed volumes of reverse osmosis water at room temperature. This was followed by elution with 5 bed volumes of 5% ethanol (by weight), again at room temperature. Finally, the column was washed in a single pass with 5 bed volumes of 100% ethanol. The elution was performed at room temperature. Each of these three fractions was collected separately. The particular order for the washing steps and the elution was selected to be in the order of the polarity of the solvents. If the order were different, an inferior result may have ensued, such as a lower yield. The first fraction using reverse osmosis water removed the most polar compounds from the resin. The hydroethanol fraction eluted compounds of lesser polarity, and the 100% ethanol solvent removed the least polar compounds. Less polar solvents could also be used to elute less polar compounds.

The 5% ethanol fraction (i.e. the purified psychoactive alkaloid solution) was then concentrated in a rotary evaporator to form 3.90 g of concentrated aqueous slurry at 30% solids, containing 195.1 mg of total alkaloids (e.g. psilocin and possibly other dephosphorylated psychoactive alkaloids). The result was a purified psychoactive alkaloid extract, in slurry form. Further, the desired amount of the psychoactive alkaloid obtained was 5.00% by weight of the slurry. Knowing this, it is possible to replace the solvent with an equivalent weight of excipients to provide a purified extract with a psychoactive alkaloid content of 5.00% dry weight.

A similar process may be used for purification of extracts that have been obtained without the dephosphorylation control.

Example 2.2: Purification with Cation Exchange and Non-Ionic Macroporous Resins

The pH of the psychoactive alkaloid extract of example 1, in aqueous form, was adjusted to a pH of 3.0 (+/−0.5) by adding 1M HCl. It was then mixed with 200 g of Amberlite® MAC-3 H, a strong cationic ion-exchange resin in its hydrogen form, to result in a filtrate-resin mixture, in which components of the psychoactive alkaloid filtrate were adsorbed onto the cation exchange resin. Psilocin's polarity is such that it is partitioned onto the resin. The pH of 3 would also ensure that psilocybin, if present, was in its protonated form, and thus also adsorbed onto the cationic exchange resin efficiently. The filtrate-resin mixture was agitated for 4 hours at room temperature (21° C.-25° C.) and then filtered. The filtrate was discarded, and the resin was rinsed with 2.0 L of 100% EtOH and then 2.0 L of $H_2O$ to remove any impurities. Finally, the psilocin (and, in other cases, psilocybin) fraction was eluted with 2.0 L of 2% HCl/80% EtOH, for 4 hours at room temperature.

The eluted fraction was brought to a pH of 4.0 (i.e. the isoelectric point of psilocybin) by adding 2M NaOH. The filtrate was then centrifuged at 3000 g to remove any solid precipitate. The resultant filtrate, in form of an aqueous solution, was then placed into a rotary evaporator and the solvent was removed until the aqueous solution reached a volume of 400 mL. The aqueous solution was then again centrifuged for 15 minutes at 3000 g to remove any solid precipitate. The supernatant was loaded onto a column of Amberlite® XAD4 macroporous resin (45.53 g of dry resin) at a flow rate of 2 bed volumes per hour. After all the 400 mL of the supernatant was loaded onto the column, it was initially washed with 5 bed volumes of reverse osmosis water, followed by elution with 5 bed volumes of 5% ethanol (by weight) and then washed with 100% ethanol. Each of these fractions was collected separately. The 5% ethanol fraction (i.e. the purified psychoactive alkaloid solution) was concentrated in a rotary evaporator to form 258 mg of solution containing 175 mg of total psychoactive alkaloids (i.e. psilocin and other dephosphorylated psychoactive alkaloids). Thus, a purified psychoactive alkaloid extract, in slurry form, with a total alkaloid concentration of 68% dry wt/wt % was obtained.

A similar process may be used for purification of extracts that have been obtained without the dephosphorylation control.

Example 2.3: Purification with Anion Exchange and Non-Ionic Macroporous Resins

The pH of the psychoactive alkaloid extract of example 1, which was in aqueous form, was adjusted to 9.5 (+/−0.5) by adding 1 M NaOH and then mixed with 150 g of Amberchrom® 50WX8 strong anionic ion-exchange resin in its hydrogen form to result in a filtrate-resin mixture, in which components of the psychoactive alkaloid filtrate were adsorbed onto the anion exchange resin. The pH of 9.5 (+/−0.5) ensured that the psychoactive alkaloids (e.g. psilocin) were deprotonated and had a net negative charge for efficient adsorption onto the strong anion exchanger.

The filtrate-resin mixture was agitated for 4 hours and then filtered out, and the filtrate was discarded. The resin was rinsed with 2.0 L of 100% EtOH and then 2.0 L of $H_2O$ to remove impurities. Finally, the psychoactive alkaloid fraction was eluted with 2.0 L of 2% NaCl/80% EtOH for 4 hours.

The eluted fraction was brought to a pH of 4.0 with the addition 2 M HCl. The extract was then centrifuged at 3000 g to remove any solid precipitate. The resultant extract, in from of a solution, was then placed into a rotary evaporator and the solvent was removed to result in a volume of 400 mL.

The resultant 400 mL aqueous solution was centrifuged for 15 minutes at 3000 g to remove any solid precipitate. The supernatant was loaded onto a column of Amberlite® XAD4 macroporous resin (45.53 g of dry resin) at a flow rate of 2 bed volumes per hour, to allow components of the supernatant to be adsorbed onto the macroporous resin. After all 400 mL of supernatant was loaded onto the column, the column was initially washed with 5 bed volumes of reverse osmosis water, followed by elution with 5 bed volumes of 5% ethanol (by weight) and then a final wash with 100% ethanol was performed. Each of these fractions was collected separately. The 5% ethanol fraction (i.e. the purified psychoactive alkaloid solution) was concentrated in a rotary evaporator to form 325 mg of solution containing 175 mg of total alkaloids (e.g. psilocin and other dephosphorylated psychoactive alkaloids). A purified psychoactive alkaloid extract, in slurry form, with a concentration of 54% dry wt/wt % of total alkaloids was therefore obtained.

A similar process may be used for purification of extracts that have been obtained without the dephosphorylation control.

Example 3.1: Psychoactive Hydrogel Patch

In this example, shown in TABLE 1, the psychoactive component is a 30% extract, i.e. a purified extract that has a psychoactive alkaloid concentration of 30% by weight. In particular, the phosphorylatable alkaloids in the extract have all been dephosphorylated during extraction. The total psychoactive alkaloid content in the hydrogel patch is 25.125 mg. After formulation, the composition needs to be dried to allow the volatile components to evaporate, in order to harden the gel.

TABLE 1

| Ingredient Type | Specific Ingredient | % | g |
|---|---|---|---|
| Psychoactive component | 30% extract | 16.75 | 0.084 |
| Carrier | Ethanol | 22 | 0.110 |
| Penetration agent 1 | DMSO (dimethylsulfoxide) | 7 | 0.035 |
| Penetration agent 2 | Propylene glycol | 15 | 0.075 |
| Penetration agent 3 | Water | 10 | 0.050 |
| Antioxidant | Ascorbic acid | 5.25 | 0.026 |
| Thickening agent 1 | hydroxypropyl-methylcellulose (HPMC) | 12 | 0.060 |
| Thickening agent 2 | Polyvinyl alcohol (PVA) | 12 | 0.060 |
| | | Total = 100 | Total = 0.500 |

Example 3.2: Psychoactive Microdose Hydrogel Patch

In this example, shown in TABLE 2, the psychoactive component is a 30% extract, i.e. a purified extract that has a psychoactive alkaloid concentration of 30% by weight. In particular, the phosphorylatable alkaloids in the extract have all been dephosphorylated during extraction. The total psychoactive alkaloid content in the hydrogel patch is 7.500 mg. After formulation, the composition needs to be dried to allow the volatile components to evaporate, in order to harden the gel.

TABLE 2

| Ingredient Type | Specific Ingredient | % | g |
|---|---|---|---|
| Psychoactive component | 30% extract | 5 | 0.025 |
| Carrier | Isopropyl alcohol | 27 | 0.135 |
| Penetration agent 1 | Propylene glycol | 17 | 0.085 |
| Penetration agent 2 | Water | 18 | 0.090 |
| Antioxidant | Citric acid | 5 | 0.025 |
| Thickening agent 1 | PVP | 8 | 0.040 |
| Thickening agent 2 | polyacrylic acid | 20 | 0.100 |
| | | Total = 100 | Total = 0.500 |

Example 3.3: Psychoactive Hydrogel Patch

In this example, shown in TABLE 3, the psychoactive component is a 30% extract, i.e. a purified extract that has a psychoactive alkaloid concentration of 30% by weight. In particular, the phosphorylatable alkaloids in the extract have all been dephosphorylated during extraction. The total psychoactive alkaloid content in the hydrogel patch is 45.000 mg. After formulation, the composition needs to be dried to allow the volatile components to evaporate, in order to harden the gel.

TABLE 3

| Ingredient Type | Specific Ingredient | % | g |
|---|---|---|---|
| Psychoactive component | 30% extract | 30 | 0.150 |
| Carrier | Ethanol | 18 | 0.090 |
| Penetration agent 1 | Propylene glycol | 11 | 0.055 |
| Penetration agent 2 | Glycerine | 5 | 0.025 |
| Penetration agent 3 | Water | 8.5 | 0.043 |
| Antioxidant | Ascorbic acid | 5 | 0.025 |
| Thickening agent 1 | HPMC | 7.5 | 0.038 |
| Thickening agent 2 | PVP | 15 | 0.075 |
| | | Total = 100 | Total = 0.500 |

Example 3.4: Psychoactive Topical Gel

In this example, shown in TABLE 4, the psychoactive component is a 30% extract, i.e. a purified extract that has a psychoactive alkaloid concentration of 30% by weight. In particular, the phosphorylatable alkaloids in the extract have all been dephosphorylated during extraction. The total psychoactive alkaloid content in the hydrogel patch is 25.125 mg. After formulation, the composition is in the form of a cream ready for packaging.

TABLE 4

| Ingredient Type | Specific Ingredient | % | g |
|---|---|---|---|
| Psychoactive component | 30% extract | 16.75 | 0.084 |
| Carrier | Ethanol | 20 | 0.100 |
| Penetration agent 1 | DMSO | 45 | 0.225 |
| Penetration agent 2 | Water | 10 | 0.050 |
| Antioxidant | Ascorbic acid | 5 | 0.025 |
| Thickening agent | PVP | 3.25 | 0.016 |
| | | Total = 100 | Total = 0.500 |

Example 3.5: Psychoactive Microdose Topical Gel

In this example, shown in TABLE 5, the psychoactive component is a 30% extract, i.e. a purified extract that has a psychoactive alkaloid concentration of 30% by weight. In particular, the phosphorylatable alkaloids in the extract have all been dephosphorylated during extraction. The total psychoactive alkaloid content in the hydrogel patch is 1.500 mg. After formulation, the composition is in the form of a cream ready for packaging.

TABLE 5

| Ingredient Type | Specific Ingredient | % | g |
|---|---|---|---|
| Psychoactive component | 30% extract | 1 | 0.005 |
| Carrier | Ethanol | 10 | 0.050 |
| Penetration agent 1 | DMSO | 75 | 0.375 |
| Penetration agent 2 | Water | 10 | 0.050 |
| Antioxidant | Ascorbic acid | 2 | 0.010 |
| Thickening agent | HPMC | 2 | 0.010 |
| | | Total = 100 | Total = 0.500 |

Example 3.6: Psychoactive Topical Gel

In this example, shown in TABLE 6, the psychoactive component is a 30% extract, i.e. a purified extract that has a psychoactive alkaloid concentration of 30% by weight. In particular, the phosphorylatable alkaloids in the extract have all been dephosphorylated during extraction. The total psychoactive alkaloid content in the hydrogel patch is 60.000 mg. After formulation, the composition is in the form of a cream ready for packaging.

TABLE 6

| Ingredient Type | Specific Ingredient | % | g |
|---|---|---|---|
| Psychoactive component | 30% extract | 40 | 0.200 |
| Carrier | Ethanol | 17 | 0.085 |
| Penetration agent 1 | Glycerine | 30 | 0.150 |
| Penetration agent 2 | Water | 7 | 0.035 |
| Antioxidant | Ascorbic acid | 5 | 0.025 |
| Thickening agent | carboxymethylcellulose sodium | 1 | 0.005 |
| | | Total = 100 | Total = 0.500 |

G. Apparatus

FIG. 4 depicts an apparatus used for obtaining a psychoactive alkaloid extract and forming a transdermal composition, resulting in a transdermal patch. In one example, raw *Psilocybe cubensis* mushrooms are added to a hopper 100 and then released in batches into container 102. The raw fungal material is then dried in a forced air oven 104 to result in the dried biomass. The dried biomass is placed into a grinder 106 for grinding to result in dried powdered biomass.

The dried powdered biomass is then placed into a heat-controlled vessel 110 and acidified solvent (S) added to the heat-controlled vessel to obtain a specific pH (lower than 3.5). The vessel 110 is surrounded by an insulating wall 108. Alternately, an insulating jacket may be wrapped around the vessel. The insulating wall 108 or jacket helps to maintain the contents 112 under a constant temperature (T) between 5-95° C. The pressure (P) inside the extraction vessel 110 may be regulated from 7 to 20,000 psi. The extraction may be performed with a solvent to solid (dried powdered biomass) proportion in the range of 1 L:1 kg to 50 L:1 kg.

After the extraction, the bottom of the extraction vessel 110 may be opened at outlet 114 and the extraction slurry collected in a container 120. The extraction slurry is then fed into a filter 122 and a first filtrate collected in container 124. The first filtrate residue 130 may then be fed back (R) into the agitated, heat-controlled vessel 110 and more solvent (S) added for a second extraction. After the second extraction, the extraction slurry may be collected in the container 120 and then fed into a filter 132. After filtration, the obtained second filtrate is collected in container 136.

After the two filtration stages, the filtrates are mixed in container 140 to obtain a mixed filtrate i.e. the psychoactive alkaloid liquid. In other embodiments, if there is only a single filtration step, this mixing step is not required. By adding a base to container 140, the pH of the psychoactive alkaloid liquid may be brought to a pH ranging from 3.5-4.5.

The pH-adjusted, mixed filtrate is then placed in a rotary evaporator 142 and part of the solvent evaporated from the mixed filtrate to form the psychoactive alkaloid extract, which is here a slurry.

The resultant slurry is then transferred to a container 144 where a measured quantity of one or more excipients is added to obtain a standardized psychoactive alkaloid composition in slurry form. The obtained standardized slurry may then be then dried to obtain the standardized psychoactive alkaloid composition.

In another example, a purified, standardized psychoactive composition may be obtained. The resultant slurry from the rotary evaporator 142 is transferred to the container 144, where the pH of the extract may be adjusted, followed by centrifugation 146 to remove the solid precipitates.

The resultant supernatant is loaded onto a column 150 of resin. An initial wash is given to the column with a solvent to remove impurities from the resin, and fraction 154 is collected. A second wash is given to the column with another solvent to elute the psychoactive alkaloids from the column and result in fraction 156. A final wash is given to the column with another solvent to wash any impurities from the column, to prepare the column for use again, and the fraction 158 is obtained. The elution fraction 156 with the psychoactive alkaloids is then concentrated in a rotary evaporator 160 to result in the purified psychoactive alkaloid solution. The solvent from the purified psychoactive alkaloid solution is then completely or partially evaporated to result in the purified psychoactive alkaloid extract 164. This extract may then be standardized by adding a measured amount of excipient to it and mixing, in container 166. If necessary, the mixture may then be dried.

The standardized, purified psychoactive composition 166 or the standardized psychoactive composition obtained in container 144 may then be mixed with an alcohol carrier and one or more permeation agents in container 166 or 144 to form the psychoactive transdermal composition. Other excipients may also be added. Care should be taken to add the thickener or gelling agent slowly, and it may be the last component to be added to the mixture. The psychoactive transdermal composition may then be used to form a patch 168, for example.

In other examples, parts of the apparatus may be reused or duplicated. For example, if desired, the elution fraction 156 may be reloaded into the container 144 for pH adjustment and the steps from thereon can be repeated to allow for further purification of the obtained purified psychoactive alkaloid solution.

H. Conclusion

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. Accordingly, the specification and drawings are to be regarded in an illustrative, rather than a restrictive, sense.

It will be clear to one having skill in the art that further variations to the specific details disclosed herein can be made, resulting in other embodiments that are within the scope of the invention disclosed. Steps in the flowchart may be performed in a different order, other steps may be added, or one or more may be removed without altering the main outcome of the processes. In some embodiments, the extract may be replaced with a synthetic psychoactive alkaloid source or composition. The process may be scaled up using larger quantities and a modified apparatus.

All parameters, dimensions, materials, quantities and configurations described herein are examples only and may be changed depending on the specific embodiment. Numbers are given to the nearest significant figure, or to 10%, whichever is the greater. Accordingly, the scope of the invention is to be construed in accordance with the substance defined by the claims.

The invention claimed is:

1. A transdermal psychoactive alkaloid composition comprising, by weight:
   1-40% of a dephosphorylated extract that comprises psilocin;
   1-30% of alcohol;
   1-80% of one or more permeation enhancers; and
   1-20% of one or more thickening agents, one or more gelling agents or both one or more thickening agents and one or more gelling agents.

2. The composition of claim 1, comprising 10-20% by weight of the dephosphorylated extract.

3. The composition of claim 1, wherein the dephosphorylated extract has a total psychoactive alkaloid content ranging from 0.1% to 99% by weight.

4. The composition of claim 1, wherein the dephosphorylated extract is a purified extract, and the purified extract has a total psychoactive alkaloid content ranging from 10% to 99% by weight.

5. The composition of claim 1, wherein the dephosphorylated extract comprises one or more naturally occurring substances from the group consisting of fats, sugars, carbohydrates, chitin, chitosan, minerals, waxes, and proteins.

6. The composition of claim 5, wherein the naturally occurring substances are present in the dephosphorylated extract in a concentration ranging from 1% to 99.9% by weight.

7. The composition of claim 1, wherein the dephosphorylated extract is from a psychoactive organism.

8. The composition of claim 1, comprising 10-20% by weight of the alcohol.

9. The composition of claim 1, wherein the alcohol is ethanol, 1-propanol, isopropyl alcohol, tert-butyl alcohol, or any combination selected therefrom.

10. The composition of claim 1, comprising 15-40% by weight of the one or more permeation enhancers.

11. The composition of claim 1, comprising 5-10% by weight of the one or more thickening agents, the one or more gelling agents or both the one or more thickening agents and the one or more gelling agents.

12. The composition of claim 1, comprising 1-5% by weight of one or more antioxidants.

13. The composition of claim 1, comprising 3-5% by weight of one or more antioxidants.

14. The composition of claim 1, comprising up to 5% by weight of one or more bioavailability enhancers.

15. The composition of claim 1, comprising 0.5-2% by weight of one or more bioavailability enhancers.

16. The composition of claim 1, wherein a total psychoactive alkaloid content in the composition is defined as a percentage to two decimal places.

17. The composition of claim 1, in a cream or a gel form.

* * * * *